(12) United States Patent
Matouk

(10) Patent No.: US 10,575,931 B2
(45) Date of Patent: Mar. 3, 2020

(54) CUSTOMIZED SINGLE PIECE DENTAL IMPLANT

(71) Applicant: Michel Matouk, Fort Lauderdale, FL (US)

(72) Inventor: Michel Matouk, Fort Lauderdale, FL (US)

( * ) Notice: Subject to any disclaimer, the term of this patent is extended or adjusted under 35 U.S.C. 154(b) by 440 days.

(21) Appl. No.: 15/355,847

(22) Filed: Nov. 18, 2016

(65) Prior Publication Data

US 2018/0140393 A1    May 24, 2018

(51) Int. Cl.
| | |
|---|---|
| A61C 8/00 | (2006.01) |
| A61C 1/08 | (2006.01) |
| A61C 9/00 | (2006.01) |
| A61C 13/00 | (2006.01) |
| A61C 13/107 | (2006.01) |

(52) U.S. Cl.
CPC ............ *A61C 8/0095* (2013.01); *A61C 1/084* (2013.01); *A61C 8/008* (2013.01); *A61C 8/0098* (2013.01); *A61C 9/0053* (2013.01); *A61C 13/0004* (2013.01); *A61C 13/0006* (2013.01); *A61C 8/0022* (2013.01); *A61C 8/0089* (2013.01); *A61C 13/0001* (2013.01)

(58) Field of Classification Search
CPC .............................................. A61C 8/00–0098
USPC ................................................. 433/172–176
See application file for complete search history.

(56) References Cited

U.S. PATENT DOCUMENTS

| | | | | |
|---|---|---|---|---|
| 4,687,443 A | * | 8/1987 | Driskell ............... | A61C 8/0018 433/173 |
| 5,527,182 A | * | 6/1996 | Willoughby .......... | A61C 8/0001 433/172 |
| 2010/0119993 A1 | * | 5/2010 | Schulter ............... | A61C 8/0066 433/173 |
| 2015/0025855 A1 | * | 1/2015 | Fisker .................. | A61C 8/0077 703/1 |

\* cited by examiner

*Primary Examiner* — Yogesh P Patel
(74) *Attorney, Agent, or Firm* — Robert M. Downey, P.A.

(57) ABSTRACT

A partially customizable single-piece dental implant includes a preformed bone-anchorage component and an abutment component that is custom milled from a block either preoperatively, (i.e., Process A) or intraoperatively, (i.e., Process B). In Process A, the planned abutment shape is designed by a computer-aided design (CAD) software based on a computerized tomographic scan and other patient data. Alternatively, under Process B, the position of the planned implant with respect to the alveolus is digitally captured (e.g., by an optical impression device or an intraoperative computerized tomographic scan). In both Process A and Process B, a blank implant having the millable block is held to allow a computer-aided manufacturing (CAM) machine to customize the abutment component, as well as part of the bone-anchorage component. The resultant dental implant is then inserted in the alveolus and either a provisional or permanent prosthesis can then be immediately loaded on the implant.

4 Claims, 8 Drawing Sheets

CUSTOMIZED SINGLE PIECE DENTAL IMPLANT

BACKGROUND OF THE INVENTION

Field of the Invention

The present invention relates to dental implants, and more particularly to a single piece implant having a pre-formed bone-anchorage component and customizable extra-bony abutment component, the shape of which is designed by computer-aided design (CAD) software followed by computer-aided manufacture (CAM) of the CAD design.

Discussion of the Related Art

Most dental implants are designed as 2-piece systems: the fixture (bone anchorage component) and the abutment (external connection to the dental implant). The 2-piece design allows for a "micro-gap" between both components that routinely has been identified as the cause of bone loss. Moreover, the repetitive replacement of transgingival components (including healing caps and abutments) to adapt to the shape of the planned restoration has been found to affect the gingival bacterial seal and the gingival architecture around the implant.

A further concern associated with 2-piece dental implants is the questionable sterility or even cleanliness of transgingival components (including healing caps and abutments). In particular, lack of sterility of 2-piece dental implant systems has been known to affect the gingival seal and the gingival architecture around the implant. The present invention solves these problems by having a sterile customized single-piece dental implant (or at least the bony anchorage component is covered to remain sterile while the customized abutment is cleaned post milling) with no micro-gap between the bone anchorage component and the abutment component.

Furthermore, most 2-piece system designs are essentially "flat-topped" while the residual dental ridge is often angled and curvaceous. The present invention solves that problem by having a customizable single-piece dental implant where the interface is designed to follow the existing ridge shape, therefore preserving that anatomy.

There are single-piece dental implants in the related art. While they solve the above problems associated with 2-piece systems, existing single-piece dental implants do not provide enough flexibility in terms of the abutment design. More specifically, existing single-piece dental implants come with a preformed abutment that is not optimal from the restorative point of view. The present invention solves that problem by providing a customized dental abutment component.

One of the ways to obtain a perfectly customized dental implant is to attempt to customize both the dental extra-bony component (i.e., abutment) and the intra-bony anchorage component. However, this creates issues of load mechanisms on the implant and the residual bone that are not well studied. Additionally, it creates the illusion of maximum biocompatibility, when in reality the implant material connection to the residual bone is very different. The present invention solves that problem by using conventional intra-bony components (conical, cylindrical tapered or otherwise) made of conventional materials and which have routinely used certain conventional thread designs and surface-texture designs. This conventional intra-bony component is fixed to a customized millable extra-bony dental abutment component that is initially in the form of a large blank (e.g., a generally cylindrical block) prior to milling to form the custom shaped abutment component.

Another issue with a fully customizable single-piece dental implant is the issue of sterility control. The present invention addresses that by one of two possible ways, either have the intra-bony surface covered during milling, or by first milling the extra-bony component followed by surface texturing, if needed, and then needed cleaning as well as sterilization.

Current dental implant systems mostly offer stock healing abutments which allow for the soft tissues to collapse during healing. The present invention allows for customized healing and final components that all have the same predetermined shape. This improves the final result.

Additionally, in current systems where early loading is used, no provision is made to accommodate any later possible gingival recession. The dental implant of the present invention provides for a vertical shoulderless margin slippage area and milled gingival component at the base of the formed abutment component to accommodate any gingival recession.

SUMMARY OF THE INVENTION

The present invention is directed to a partially customizable single-piece dental implant. The single-piece dental implant includes a preformed bone-anchorage component and an abutment component that is custom milled from a block either preoperatively, (i.e., Process A) or intraoperatively, (i.e., Process B). In Process A, the planned abutment shape is designed by a computer-aided design (CAD) software based on a computerized tomographic scan. Alternatively, under Process B, the position of the planned implant with respect to the alveolus is digitally captured (e.g., by an optical impression device or an intraoperative computerized tomographic scan). In both Process A and Process B, a blank implant, having the millable block, is held to allow a computer-aided manufacturing (CAM) machine to customize the abutment component, as well as part of the bone-anchorage component. The resultant dental implant is then inserted in the alveolus and either a provisional or permanent prosthesis can then be immediately loaded on the implant.

Objects and Advantages of the Invention

Considering the forgoing, it is a primary object of the present invention to provide a customizable single-piece dental implant that creates no microgap or discernible interface between the intra-bony anchorage component and the extra-bony abutment component.

It is a further object of the present invention to provide a customizable single-piece dental implant that incorporates a reasonably efficient modification to current dental implant manufacturing processes so that existing dental implant manufacturers can continue to use their existing intra-bony designs including shape, length, width, geometry and surface texture, thereby also allowing most surgeons to continue using their existing drilling protocols.

It is still a further object of the present invention to provide a customizable single-piece dental implant that is able to use current CAD/CAM systems.

It is a further object of the present invention to provide a customizable single-piece dental implant and method of customization that is an attractive and easily understandable advance from the dental practitioner's perspective.

It is still a further object of the present invention to provide a customizable single-piece dental implant that creates no micromovement or microgap, thereby reducing postoperative bone loss.

It is still a further object of the present invention to provide a customizable single-piece dental implant that supports interdental bone and gingiva.

It is still a further object of the present invention to provide a customizable single-piece dental implant wherein no abutment preparation is needed in the mouth (e.g., no heat, no shavings).

It is still a further object of the present invention to provide a customizable single-piece dental implant that reduces prosthetic cost and armamentarium.

It is yet a further object of the present invention to provide a customizable single-piece dental implant that provides reduced surgical armamentarium.

It is yet a further object of the present invention to provide a customizable single-piece dental implant that provides for precise and immediate provisional or final crown construction.

It is yet a further object of the present invention to provide a customizable single-piece dental implant that uses non-radiologic intraoperative 3D localization with respect to important anatomic structures.

It is still a further object of the present invention to provide a customizable single-piece dental implant that allows for a digital record of impression so that a crown can be easily duplicated if fractured.

These and other objects and advantages of the present invention are more readily apparent with reference to the following detailed description taken in conjunction with the accompanying drawings.

BRIEF DESCRIPTION OF THE DRAWINGS

For a fuller understanding of the nature of the present invention, reference should be made to the following detailed description taken in conjunction with the accompanying drawings in which.

Like reference numerals refer to like parts throughout the several views of the drawings.

DETAILED DESCRIPTION OF THE PREFERRED EMBODIMENT

A partially customizable single-piece dental implant and a system for such a device is shown throughout the several views of the drawings. The single-piece dental implant is generally indicated as 10 in FIGS. 2A-3B and includes a bone-anchorage component 20 that is pre-formed and a milled dental-abutment component 35 that is custom-milled, either preoperatively (Process A) or intraoperatively (Process B), from a millable block 30. In Process A, the planned abutment shape is designed by a computer-aided design (CAD) software based on a computerized tomographic scan. In Process B, the position of the planned implant with respect to the alveolus is digitally captured, for example by an optical impression device (or by an intraoperative computerized tomographic scan). The blank implant is held, without affecting the surface microtexture, to allow a computer-aided manufacturing (CAM) machine to customize the dental abutment component 35 from the millable block 30, as well as a part of the anchorage component 20. The resultant dental implant 10 is then inserted in the alveolus. Immediate provisionalization or loading of the prosthesis is then possible.

Figure 1:
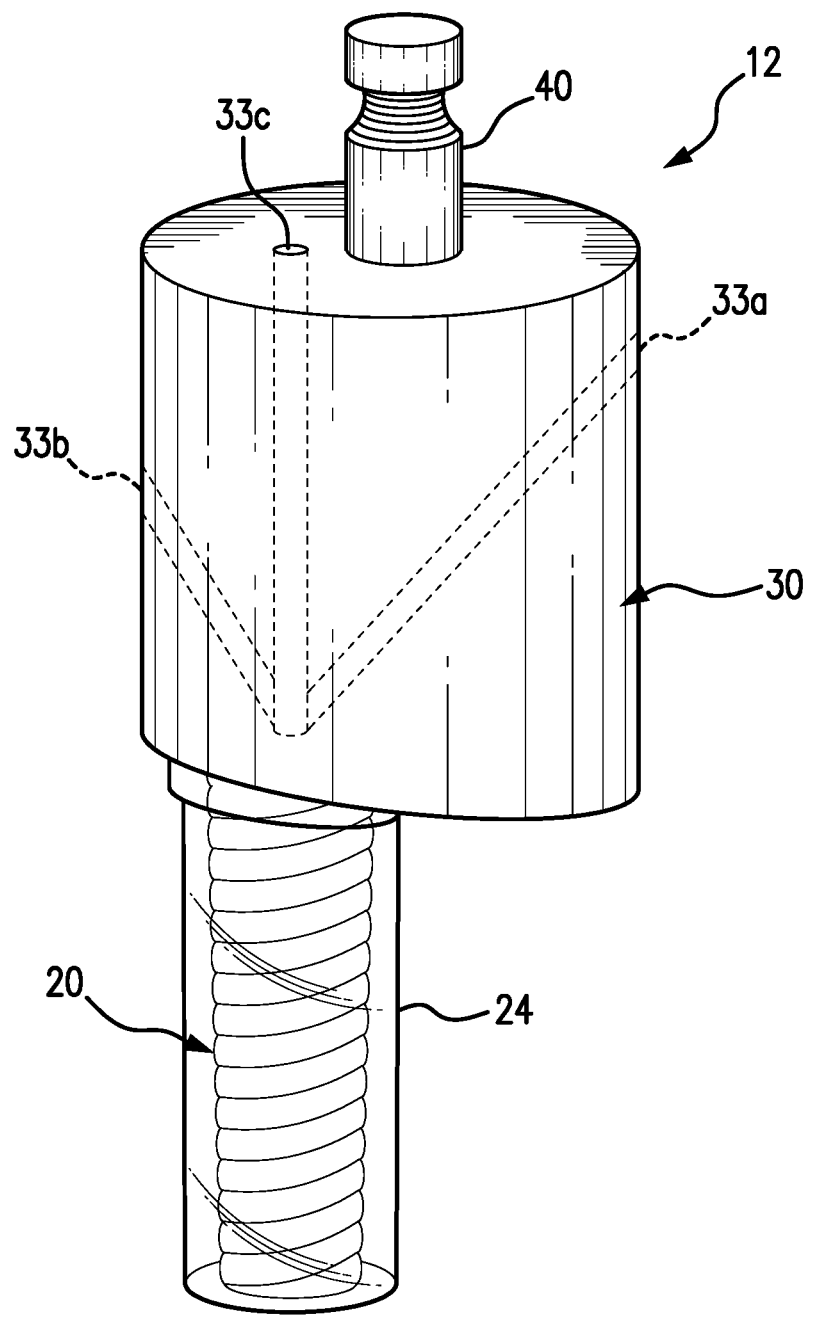
FIG. 1 is a side perspective view of the customizable single-piece implant of the present invention shown with an abutment blank prior to milling and also showing an optional surface container fitted over the intra-bony anchorage component.
Figure 2A:
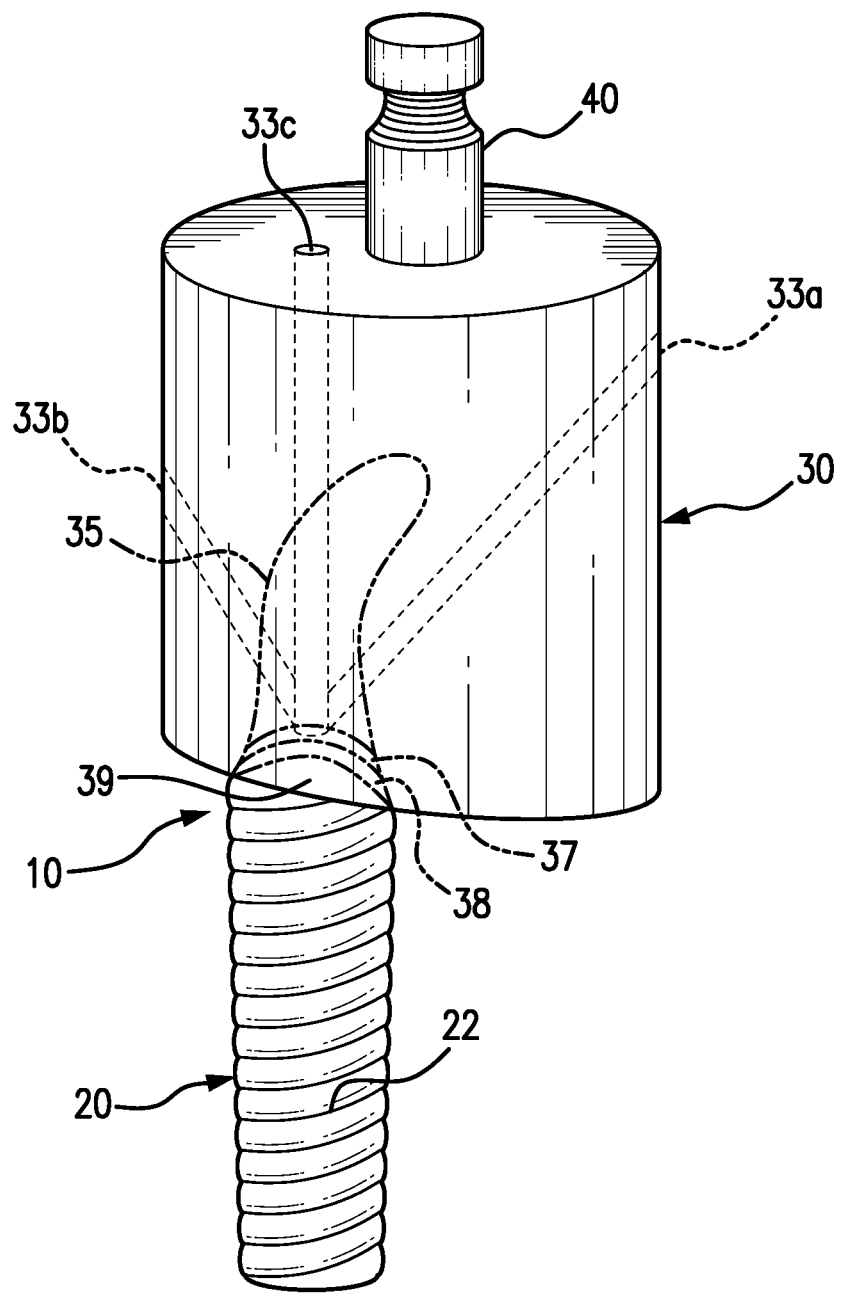
FIG. 2A is a side perspective view of the customizable single-piece implant shown with the millable abutment blank and further illustrating the desired formed shape of the abutment component (shown in broken lines) after the abutment blank has been milled.
Figure 2B:
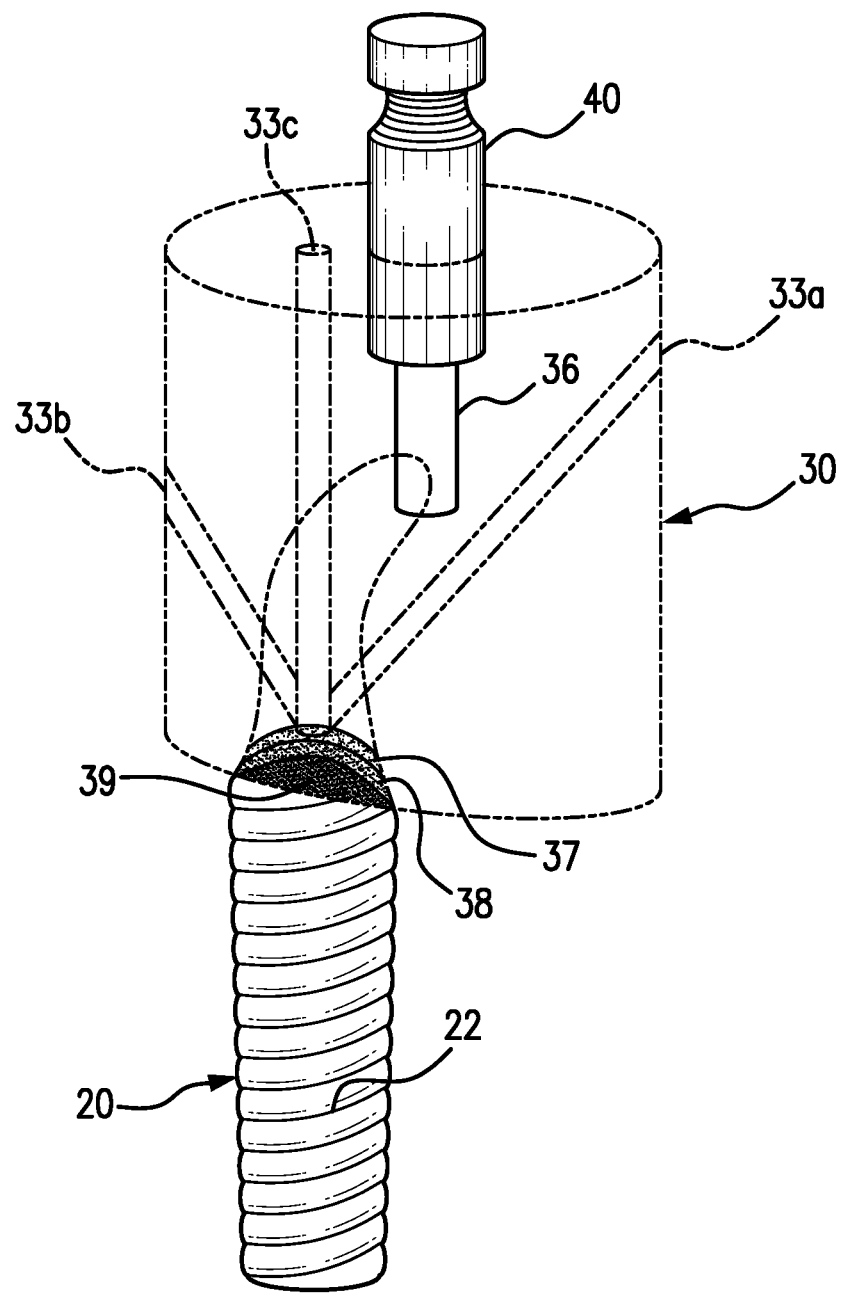
FIG. 2B is a side perspective view showing the customizable single-piece dental implant with the custom formed dental abutment component, and wherein the milled away abutment blank is shown in broken lines.

Referring to FIG. 1, the customized single-piece dental implant is created from an implant blank 12 that includes the intra-bony (i.e., bone-anchorage) component 20 and the millable block 30 which is fixed to the intra-bony component 20. The bone-anchorage component 20 may be conical, cylindrical, tapered or otherwise formed with conventional routinely used shapes and configurations with conventional thread designs 22 and surface texture designs using conventional materials. The implant blank 12 further includes a CAM insert 40 concentrically, or asymmetrically, fitted within a top end of the millable block 30. An arrangement of threaded channels are potentially provided through the millable block and may include a vertical threaded channel 33c that is centered with the bone-anchorage component, as well as eccentrically placed and angled threaded channels 33a and 33b (0-30 Degrees) lingual and/or buccal. A surface container 24 may be fitted over the bone-anchorage component 20 for purposes of sterility during milling of the block 30 to form the milled abutment 35, as seen in FIGS. 2A-3A.

Referring to FIGS. 2A-3A, the abutment component 35 of the customized single-piece implant is milled from the millable block 30 by a CAM to form the milled abutment component 35 along with, if planned by the surgical or dental provider, a margin slippage area 37, a milled gingival component 38 and a milled intra-bony component 39 between the milled abutment component 35 and the bone-anchorage component 20.

The CAM insert 40 extends down into the millable block 30 and, during the CAM machining process, a milled abutment holder 36 extending between the CAM insert 40 and the milled abutment 35 is formed to maintain a connection between the CAM insert 40 and the milled abutment 35 during the entire CAM milling process.

Figure 3A:
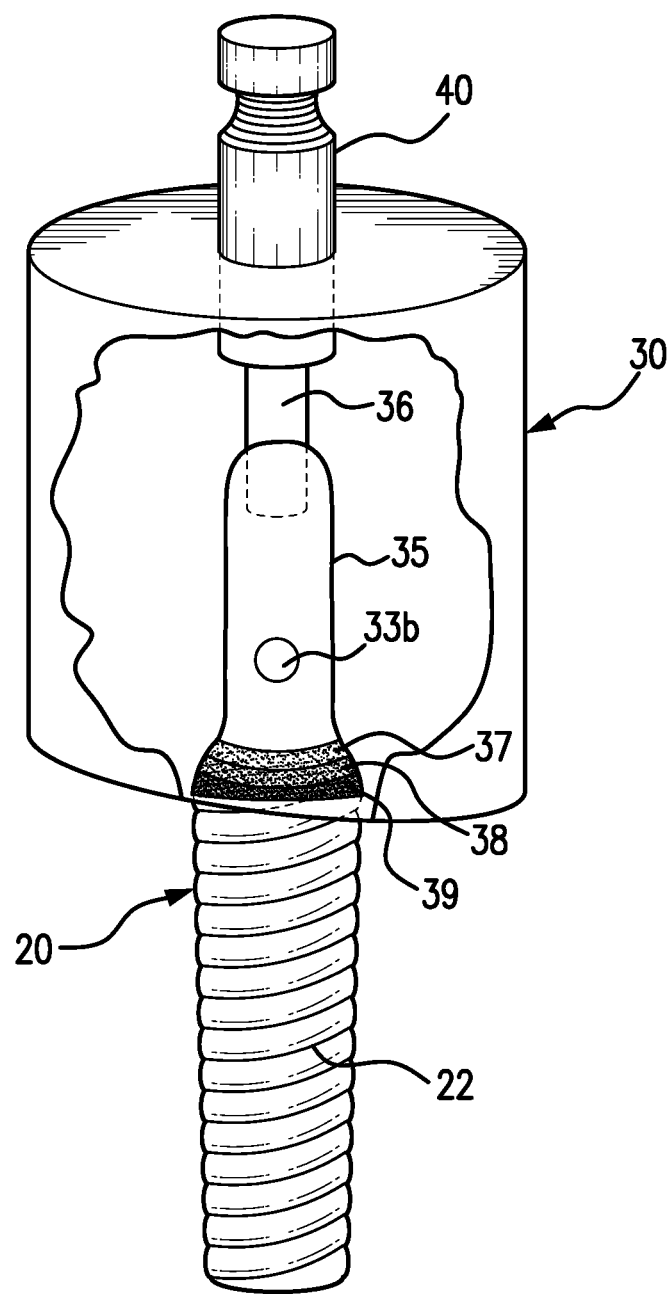
FIG. 3A is a front perspective view, shown in partial cutaway, illustrating the customizable single-piece dental implant once the abutment has been milled, but still held with the milled abutment holder.
Figure 3B:
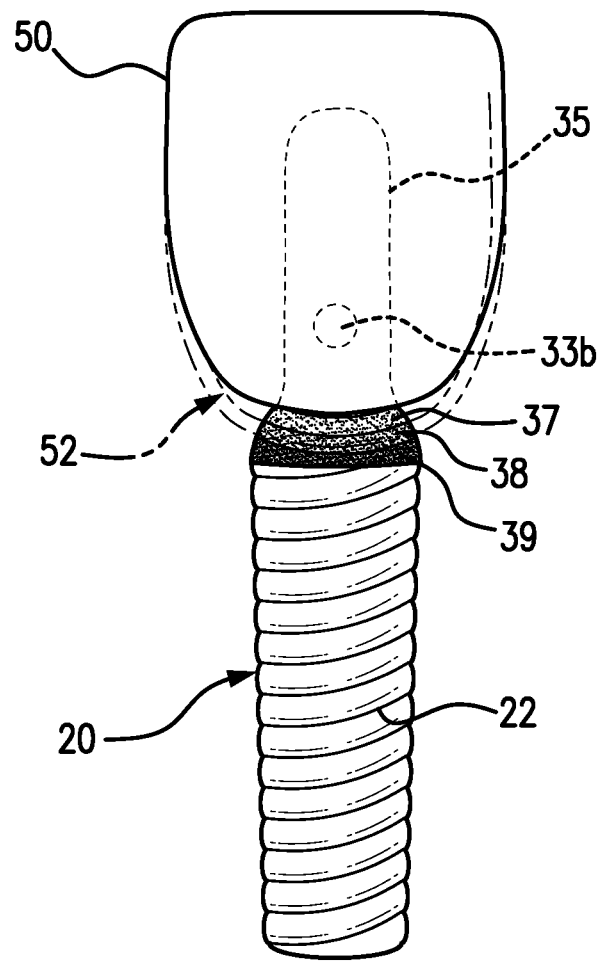
FIG. 3B is a front elevational view showing the customizable single-piece dental implant with a provisional prosthesis fitted to the abutment component, and further illustrating the extension of a permanent prosthesis in broken lines extending through an optional margin slippage area and milled gingival component.
Figure 4:
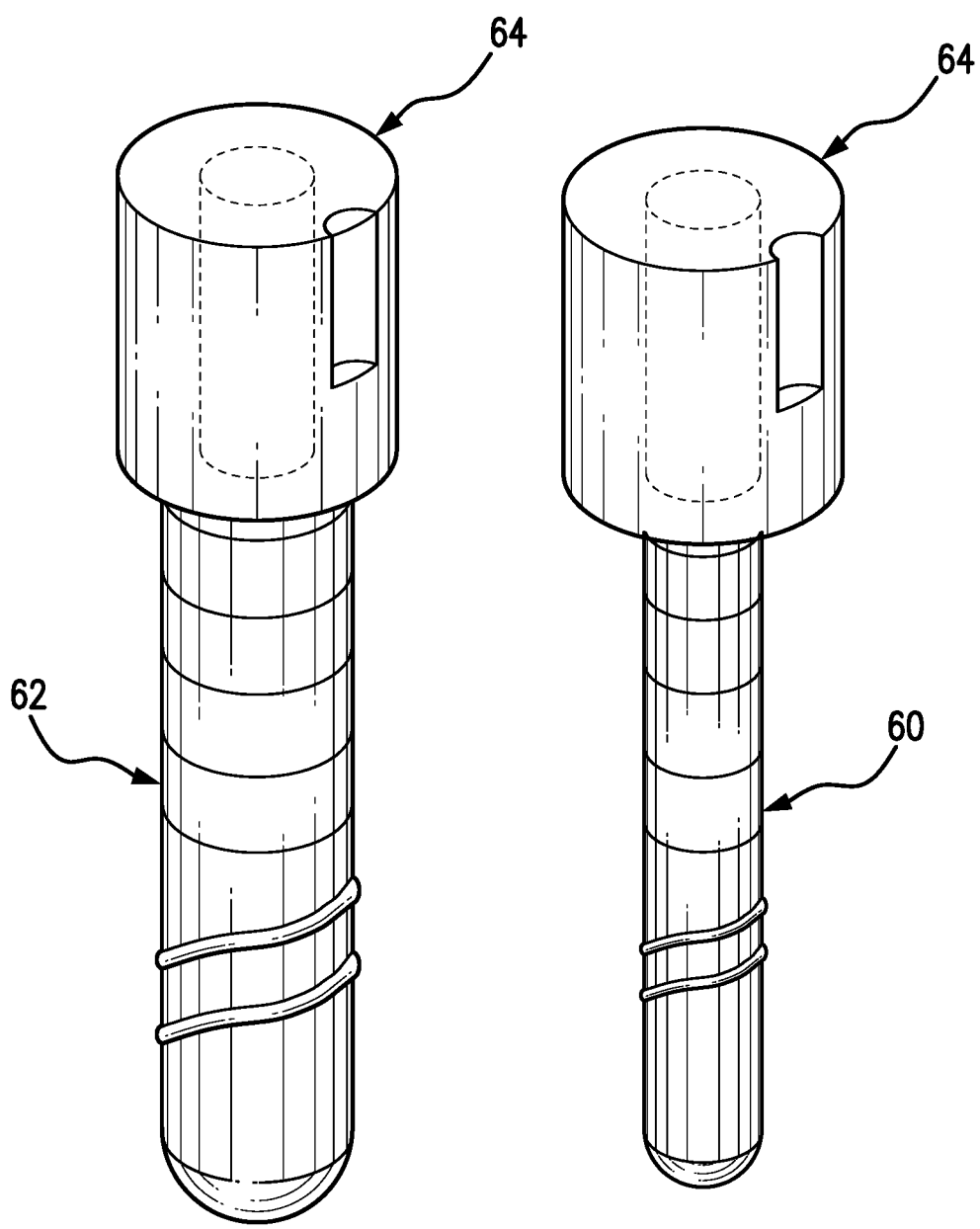
FIG. 4 is a front perspective view showing two different size modifiable scanable depth guides for use in accordance with a Process B of the invention.
Figure 5:
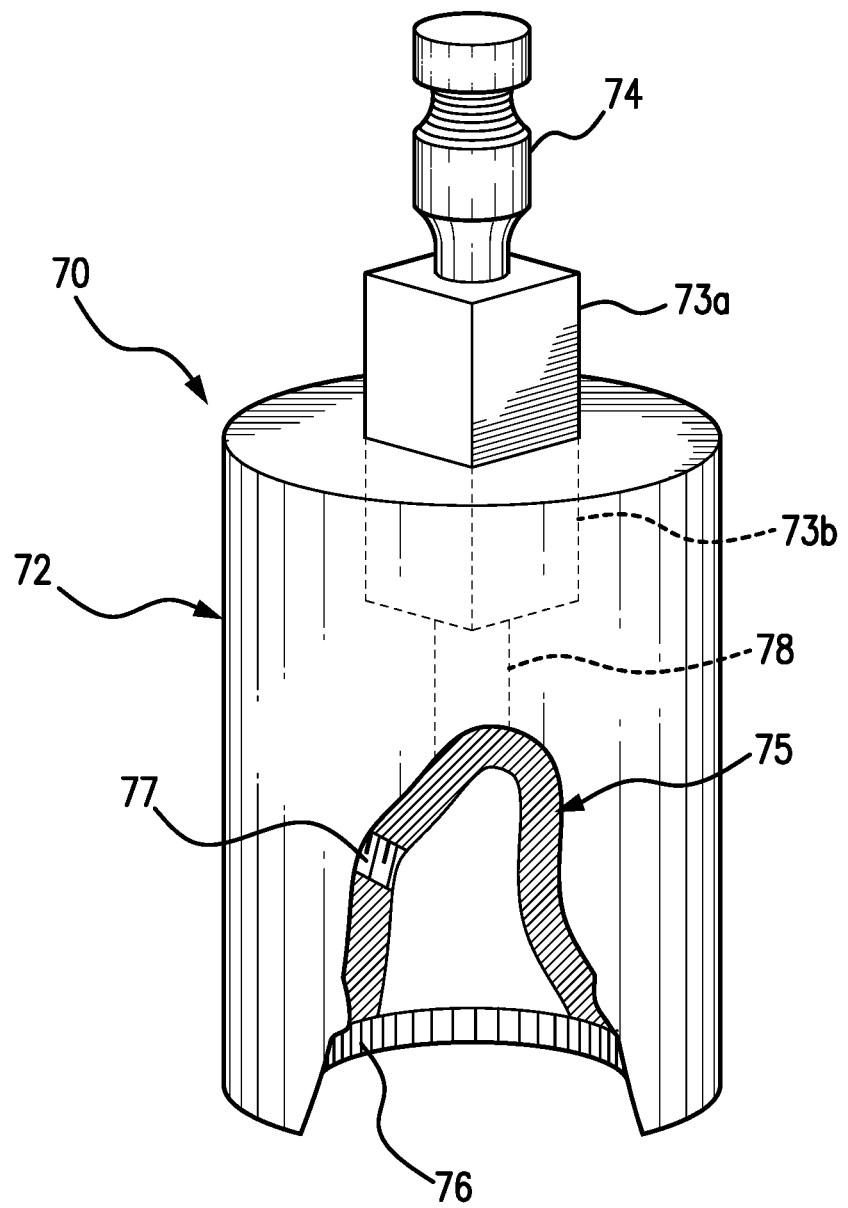
FIG. 5 is a side, top perspective view, shown in partial cutaway, illustrating a milled healing cap while still attached to the implant insertion tool.

As seen in FIG. 3B, the final customized single-piece dental implant 10 is adapted to receive both a provisional crown prosthesis 50 and, thereafter, a final crown prosthesis 52 (as indicated by the broken lines). As seen in FIG. 3B, the final prosthesis 52 may need to be extended further down (or apically) to accommodate for healing and settling of the gingival tissue after the healing period. This is allowed by the margin slippage area 37. If there are no gingival changes during healing, then the margin slippage area 37 becomes part of the milled gingival component 38; and vice versa, if an excessive amount of gingival recession occurs, then the margin slippage area 37 may need to be extended onto the milled gingival component 38.

Process A

Figure 6:
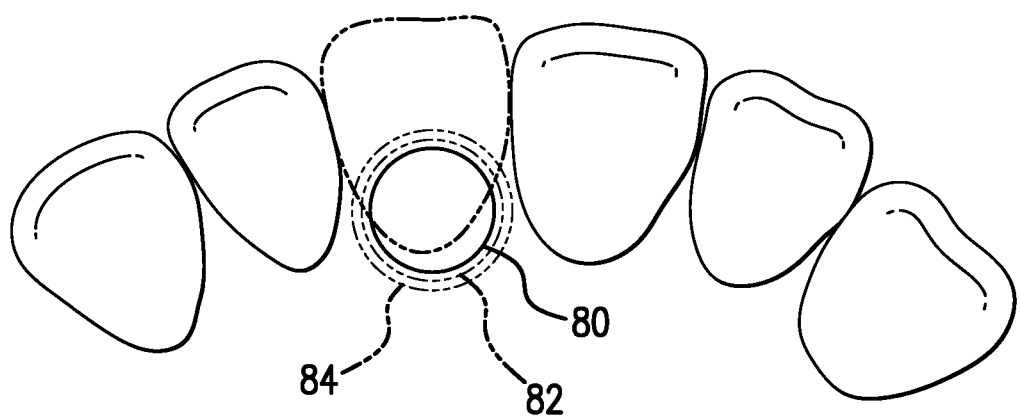
FIG. 6 is a diagram of a section of teeth of a patient illustrating the rotational clearance while placing an implant in a particular tooth site.

A method of preparing a custom dental implant 10 comprises the following steps according to a first embodiment under Process A:

1. The replacement tooth or teeth are designed (top-down design). This is done using a computer planning software and a digitalized model of the dentition or using an optical impression device.
2. The planned abutment preparation 35 is designed.
3. The new implant position is determined. This is done using a computer planning software (an example of which is described in U.S. Pat. No. 8,582,870) and a preoperative computerized tomographic scan.
4. The surgical and dental plans are approved by the surgical provider and dental provider. The intra-bony component 20 design and the osteotomy may be either tapered, cylindrical, stepped or whichever shape the implant manufacturer offers.
5. Surgical stents are fabricated to guide the surgical placement of the implant, including depth and angle control. Examples of such devices can be found in the following U.S. Pat. Nos. 8,585,402; 8,523,566; 8,794,964; and 8,398,396.
6. A selected single-piece implant blank 12 with the bone-anchorage component 20 covered by container 24 or carefully held is introduced in a computerized milling machine for CAM (computer-aided manufacturing):
   a. The selection of the implant blank 12 is mostly from among a range of depths, widths and shapes for the intra-bony component 20. Potentially abutment angulation can be designed. Angulation of the abutment must allow for rotational clearance 82 (see FIG. 6) from other structures, along with the planned holder 75 and its rotational clearance 84, during implant insertion as illustrated in FIG. 6 (unless implant is potentially tapped in place). Also, potentially a tooth-compatible colored structure for the dental component may be provided in a one-piece but two material design (in this design the bone anchored component 20 is in one material, such as a titanium alloy, and the abutment blank 30 is fused to it but is in another material, such as zirconium) as long as no microgap or discernible interface is created.
   b. The single piece implant 10 may be fabricated from any material, or combination of materials, that is suitable for dental implantation (eg: Titanium oxide, Titanium based alloys, zirconium oxide, zirconium based alloys and other suitable materials).
   c. The design can include one or a plurality of internally threaded screw channels 33a-33c:
      i. One or some of the screw channels 33a-33c can be centered on the implant (e.g., 33c) or eccentrically placed and angled (0-30°) lingual (e.g., 33a) and/or buccal (e.g., 33b).
      ii. One or a plurality of the internally threaded screw channels facilitate implant salvage in case the abutment design later needs changing or the implant needs to be removed.
      iii. Any of the internally threaded screw channels 33a-33c can potentially be used for screw retention of the dental restoration if a screwed-in restoration is desirable (versus a cemented restoration). In some rare cases when none of the preplanned channels can be used for screw retention of the restoration, a new threaded channel can potentially be milled during or after the abutment milling.
      iv. Any of the internally threaded screw channels 33a-33c can potentially be used for implant insertion in the bone (this option will usually only be viable in sites where larger implants are placed, such as posterior teeth, to allow for a thick enough channel that can withstand insertional torque).
      v. When implant dimensions are larger, a counter rotational feature can potentially be added (or milled) close to the surface of the planned abutment to provide for prosthetic flexibility.
   d. Sterility is guaranteed by one of two possible ways, either by having the intra-bony surface covered by a cover or container 24 during the milling (Process A-1), probably up to the first thread away from the abutment or, simpler, by first milling the extrabony component on a textured implant followed by final surface texturing, if needed, and then needed cleaning as well as sterilization (Process A-2). Process A-2 guarantees the best quality control and is the preferred embodiment.
7. The non-anchorage components 35, 37-39 are milled as designed:
   a. If any part of the milled area will remain intra-bony (i.e., 39) based on the preoperative imaging, then the surface is machined smooth, or preferably textured in a way comparable to the rest of the intra-bony component (easiest in process A-2).
   b. A small part of the milled area will potentially remain deep sub-gingival 38, this is also milled to support the gingiva and either machined smooth or textured as needed (also easiest in process A-2).
   c. The extra-gingival component, called the milled abutment 35, which will support the planned crown 50, also potentially extends superficially under the gingiva to hide the interface from the milled component for aesthetic reasons.
   d. The margin of the planned crown 50 can be designed with a vertical/shoulderless type preparation allowing for the later final crown 52 margin to be placed more apically. This is in case gingival recession occurs after placing the transitional crown or the planned crown 50. The area that can be used for margin placement, the margin slippage area 37, is usually 0.5-1 mm to allow for such possible recession.
8. A second millable block 72 on an insertion tool blank 70 with a cam insert 74 and an insertion handle 73a is milled as a negative (or female) of the previously milled abutment to provide an insertion tool that allows for an easy holder to place the single-piece dental implant 10 in the mouth. That same block, or alternatively additional negatives (or females) of the final abutment shape, can be used to provide a healing cap 75 that is smooth and undercontoured in the extragingival areas, but fully contoured in the gingival areas 76 to support the gingival complex healing:
   a. If the milled healing cap 75 and its handle 73a-73b/holder 78 complex is fabricated from a strong enough material that withstands adequate rotational torsional forces (e.g., >35 Ncm), then it can be used to seat the implant intra-bony component 20.
   b. If the complex of the milled healing cap 75 and its handle/holder 73a, 73b, 78 is not strong enough based on the material selected for fabrication and its dimensions (this can be noted part of the CAD software), then an additional premilled stronger insertion block can be fabricated to help seat the implant.
   c. The first option of the milled healing cap 75 being used to seat the implant is the preferred embodiment as it would allow for a multi-use component as follows:
      i. It helps to seat the implant intra-bony component 20 as part of the healing cap 75, handle/holder 73a, 73b, 78 complex.
      ii. It helps to note the final direction using potentially the threaded channel marker 77.
      iii. It provides customized gingival support 76 during healing.
      iv. It is used as the intaglio surface of the temporary prosthesis, which can also be milled to be cemented on top of this component, with some degree of looseness to allow for minimal implant malposition. Once cemented, the gingival support portion 76 will bring the margins clearly supragingival to allow for adequate cleansing.
9. The guides, pre-milled dental implant(s), pre-milled healing cap(s) if needed, premilled transitional restoration(s) if needed, and pre-milled insertion block(s) are delivered to the surgical provider.
10. The implant osteotomy is performed using well known guided surgery techniques.
11. The customized single-piece dental implant 10 is inserted as planned:
   a. CAM will include buccal mark, preferably one of the threaded channels 33a-33c or some other guide or notch as to alignment, to guide the surgical provider with some degree of rotation allowed in prep.
   b. Ideally, the single-piece dental implant 10 is inserted using the CAD/CAM fabricated insertion tool which should also have a buccal mark 77 or notch to help with alignment.
   c. Alternatively (especially if the planned abutment 35 is too circular), a standardized grooved design is potentially milled in the abutment 35 or prefabricated between the implant intra-bony component 20 and the block 30 or another tool held by a holding screw through the threaded channel is used to screw in the implant intra-bony component 20.
   d. Alternatively, when large enough implants are used, one of the internally threaded screw channels 33a-33c can be used to hold an internal insertion device.
12. The provisional 50 or final 52 crown restoration(s) can potentially also be computer-milled:
   a. In connected multi-implant cases or in cases where rotational or depth changes from the plan have occurred, a seating guide or a second optical scan may need to be done prior to restoration milling to accommodate for rotational changes during insertion.
   b. Alternatively, the provisional crown 50 may be fabricated to fit (slightly loosely) over the healing cap 75 with the margin between the two surfaces preferably supergingival. This allows for cementation to make up for slight rotational and depth changes. A transparent or perforated test provisional crown may also be provided, upon request, to allow for testing clearance to modify the intaglio surface of the provisional in case that is needed.
13. If bony quality and implant primary stability are adequate, the transitional crown restoration(s) is placed.

Process B

A method of preparing a custom single-piece dental implant 10, comprises the following steps according to a second embodiment under Process B:
1. The replacement tooth or teeth are designed (top-down design). This can potentially be done using a computer planning software and a digitalized model of the dentition or using an optical impression device.
2. The planned abutment preparation 35 is designed:
   a. If the CAD (computer-aided design) component was not preoperatively done (eg: broken incisor); then a CAD tooth from the CAD library (prior art) is used or, potentially a radiopaque hollowed tooth can be used as a CAD guide.
3. The new implant position is determined. This is potentially done using a computer planning software (an example of which is described in U.S. Pat. No. 8,582,870) and a preoperative computerized tomographic scan.
4. The surgical and dental plans are potentially approved by the surgical provider and dental provider. The intrabony component 20 design and the osteotomy may be either tapered, cylindrical, stepped or whichever shape the implant manufacturer offers.
5. Surgical stents are potentially fabricated to guide the surgical placement of the implant, including depth and angle control. Examples of such devices can be found in the following U.S. Pat. Nos. 8,585,402; 8,523,566; 8,794,964; 8,398,396.
6. The implant osteotomy is performed (the shape of the osteotomy is determined by the shape of the prefabricated intra-bony part that best fits the plan above), this can potentially be aided by well-known guided surgery techniques.
7. A final depth guide 62 is placed and slightly tightened using the partial and gently threaded design (i.e., the pitch of the threads should be less than the planned final implant threads).
8. The position of the depth guide 62 is digitally captured using well known optical intra-oral scanners and a scan body 64 attached to the depth guide:
   a. If position is not finalized, an initial depth guide 60 with scan body 64 is placed after one of the initial twist drills for that implant system. The implant planned position captured by optical intra-oral scanning of the initial depth guide 60 can be merged with the preoperative CT (computerized tomography or other imaging) to predict location with respect to important anatomic structures once the full size implant is placed. Optical intraoral scanning is done either with an intraoral scanner (such as US20120135371 A1) where the scan body 64 is attached to the initial guide 60 or using an attachment other than the scan body 64 so that the position can be identified with a surgical navigation system (such as that in US20140147807 A1).
  b. If a plurality if implants are being placed, then multiple depth guides are potentially captured simultaneously using the optical scanner and the attached scan bodies 64 or using the navigation system attachments as above.
9. The actual abutment 35, which might be slightly different from the pre-planned one due to implant position variation, is designed:
  a. If a plurality if implants are being placed, the design compensates for angulation problems.
  b. The bone level is also determined at this point to help design the milled intra-bony component 39:
    i. It can potentially be scanned intraoperatively (in an open incision design), this is part of the preferred embodiment for process B.
    ii. It can be noted by merging the optical scan with the preoperative computerized tomography scan.
    iii. Or, in a closed incision where the computerized tomography scan is not readily merged, it is potentially possible to just set depth of bone on optical scan based on well-known appropriate biological width parameters (e.g., 2 mm deeper than preoperative gum level all around except 3.5 mm on buccal).
10. A selected single-piece implant blank 12 (FIG. 1) with the bone-anchored component 20 covered for sterility (e.g., a shrink wrap that can be drilled out or preferably in a container 24 that goes to the last planned thread) or carefully held with sterile holders is introduced in a computerized milling machine for CAM (computer-aided manufacturing):
  a. The selection of the implant blank 12 mostly takes into account range of depths, widths and shapes for the intra-bony component 20. Potentially abutment angulation can be designed. Angulation of the abutment must allow for rotational clearance 82, along with the planned holder 75 and its rotational clearance 84, during implant insertion from other structures, as illustrated in FIG. 6 (unless implant is potentially tapped in place). Also, potentially a tooth-compatible colored structure for the dental component may be provided in a one piece but two material design (in this design the bone anchored component 20 is in one material, such as a titanium alloy, and the abutment blank 30 is fused to it but is in another material (such as zirconium)) as long as no microgap or discernible interface.
  b. The single piece implant 10 may be fabricated from any material, or combination of materials, that is suitable for dental implantation (e.g., Titanium oxide, Titanium based alloys, zirconium oxide, zirconium based alloys and other suitable materials).
  c. The design can include one or a plurality of internally threaded screw channels 33a-33c:
    i. One or some of the screw channels can be centered on the implant (e.g., 33c) or eccentrically placed and angled (0-30°) lingual (e.g., 33a) and/or buccal (e.g., 33b).
    ii. One or a plurality of the internally threaded screw channels facilitate implant salvage in case the abutment design later needs changing or the implant needs to be removed.
    iii. Any of the internally threaded screw channels 33a-33c can potentially be used for screw retention of the dental restoration if a screwed-in restoration is desirable (versus a cemented restoration). In some rare cases when none of the preplanned channels can be used for screw retention of the restoration, a new threaded channel can potentially be milled during or after the abutment milling.
    iv. Any of the internally threaded screw channels 33a-33c can potentially be used for implant insertion in the bone (this option will usually only be viable in sites where larger implants are placed, such as posterior teeth, to allow for a thick enough channel that can withstand insertional torque).
    v. When implant dimensions are larger, a counter rotational feature can potentially be added (or milled) close to the surface of the planned abutment to provide for prosthetic flexibility.
  d. Sterility is provided by having the intra-bony surface covered by a cover or container 24 during milling probably up to the first thread away from the abutment.
11. The non-anchorage components are milled as designed:
  a. If any part of the milled area will remain intra-bony (i.e., 39) based on the preoperative imaging, then the surface is machined smooth, or preferably textured in a way comparable to the rest of the intra-bony component.
  b. A small part of the milled area will potentially remain deep sub-gingival 38, this is also milled to support the gingiva and either machined smooth or textured as needed.
  c. The extra-gingival component, called the milled-abutment 35, which will support the planned crown 50, also potentially extends superficially under the gingiva to hide the interface from the milled component for esthetic reasons.
  d. The margin of the planned crown 50 can potentially be designed with a vertical/shoulderless type preparation allowing for the later final crown 52 margin to be placed more apically. This is in case gingival recession occurs after placing the transitional crown or the planned crown 50. The area that can be used for margin placement, the margin slippage area 37, is usually 0.5-1 mm to allow for such possible recession.
12. A second millable block 72 on an insertion tool blank 70 with a cam insert 74 and an insertion handle 73a is milled as a negative (or female) of the previously milled abutment to allow for an easy holder to place the single-piece dental implant 10 in the mouth. That same block, or alternatively additional negatives (or females) of the final abutment shape, can be used to provide a healing cap 75 that is smooth and undercontoured in the extragingival areas, but fully contoured in the gingival areas 76 to support the gingival complex healing:
  a. If the milled healing cap 75 and its handle 73a-73b/holder 78 complex is fabricated from a strong enough material that withstands adequate rotational torsional forces (e.g., >35 Ncm), then it can be used to seat the implant intra-bony component 20.
  b. If the complex of the milled healing cap 75 and its handle/holder 73a, 73b, 78 is not strong enough based on the material selected for fabrication and its dimensions (this can be noted part of the CAD software), then an additional premilled stronger insertion block can be fabricated to help seat the implant.
  c. The first option of the milled healing cap 75 being used to seat the implant is the preferred embodiment as it would allow for a multi-use component as follows:
    i. It helps to seat the implant intra-bony component 20 as part of the healing cap 75, handle/holder complex 73*a*, 73*b*, 78.
    ii. It helps to note the final direction using potentially the threaded channel marker 77.
    iii. It provides customized gingival support 76 during healing.
    iv. It is used as the intaglio surface of the temporary prosthesis, which can also be milled to be cemented on top of this component, with some degree of looseness to allow for minimal implant malposition. Once cemented, the gingival support portion 76 will bring the margins clearly supragingival to allow for adequate cleansing.
13. The customized single-piece dental implant 10 is inserted as planned:
  a. CAM will include buccal mark, preferably one of the threaded channels 33*a*-33*c* or some other guide or notch as to alignment, to guide the surgical provider with some degree of rotation allowed in prep.
  b. Ideally, the single-piece dental implant 10 is inserted using the CAD/CAM fabricated insertion tool.
  c. Alternatively (especially if the planned abutment 35 is too circular), a standardized grooved design is potentially milled in the abutment 35 or prefabricated between the implant intra-bony component 20 and the block 30 or another tool held by a holding screw through the threaded channel is used to screw in the implant intra-bony component 20.
  d. Alternatively, when large enough implants are used, one of the internally threaded screw channels 33*a*-33*c* can be used to hold an internal insertion device.
  e. If the implant is too-rotated (possibly deeper seating than expected) then a few possible salvage options exist:
    i. Can use a standard 2-piece abutment and dental implant.
    ii. Can re-scan and capture location of buccal notch to help in re-milling another implant.
14. The provisional 50 or final 52 crown restoration(s) can potentially also be computer-milled:
  a. In connected multi-implant cases or in cases where rotational or depth changes from the plan have occurred, a second optical scan may need to be done prior to restoration milling to accommodate for rotational changes during insertion.
  b. Alternatively, the provisional crown 50 may be fabricated to fit (slightly loosely) over the healing cap 75 with the margin between the two surfaces preferably supergingival. This allows for cementation to make up for slight rotational and depth changes. A transparent or perforated test provisional crown may also be provided, upon request, to allow for testing clearance to modify the intaglio surface of the provisional in case that is needed.
  15. If bony quality and implant primary stability are adequate, the transitional crown restoration(s) is placed.

While the present invention has been shown in accordance with a preferred and practical embodiment, it is recognized that departures from the instant disclosure are fully contemplated within the spirit and scope of the present invention which is not to be limited except as defined in the following claims.

What is claimed is:

1. A customizable single-piece dental implant comprising:
   a one-piece implant blank comprising:
      a bone-anchorage component having external threads and an external surface texture;
      a millable block on a top end of the bone-anchorage component, and the millable block and bone-anchorage component defining a unitary, one-piece body, and the millable block being structured and disposed to be milled by a computer-aided manufacturing machine to form a custom milled abutment component that is integral with the bone-anchorage component, and the millable block is configured to be milled by the computer-aided manufacturing machine (CAM) to provide a shoulderless margin slippage area at a base of the custom milled abutment component to allow for gingival recession; and
      a CAM insert member extending from a top end of the millable block, and the CAM insert member is configured to be held by the computer-aided manufacturing machine during milling of the millable block to form the custom milled abutment component, wherein the millable block includes a plurality of threaded channels extending at least partially therethrough and at various angles relative to one another.

2. The customizable single-piece dental implant as recited in claim 1 further comprising:
   a healing cap blank comprising:
      a millable block structured and disposed to be milled by a computer-aided manufacturing machine to form a milled healing cap for congruent receipt of the custom milled abutment component therein; and
      a CAM insert member extending from a top end of the millable block, and the CAM insert member is configured to be held by the computer-aided manufacturing machine during milling of the millable block to form the milled healing cap.

3. The customizable single-piece dental implant as recited in claim 1 wherein the millable block is configured to be milled by the computer-aided manufacturing machine to provide a gingival component below the milled shoulderless margin slippage area.

4. The customizable single-piece dental implant as recited in claim 3 wherein the millable block is configured to be milled by the computer-aided manufacturing machine to provide a milled intra-bony component below the gingival component.

* * * * *